United States Patent [19]
Per-Lee

[11] Patent Number: 5,388,700
[45] Date of Patent: Feb. 14, 1995

[54] APPLICATOR DEVICE

[76] Inventor: Myra S. Per-Lee, 12405 Floresta Way, San Diego, Calif. 92128

[21] Appl. No.: 107,510
[22] Filed: Aug. 17, 1993
[51] Int. Cl.6 ............................................. A45D 40/26
[52] U.S. Cl. .................................. 206/581; 206/229; 132/320; 15/118; 15/244.3
[58] Field of Search ........................... 128/67; 132/320; 15/209.1, 210.1, 244.3, 118, 244.1, 244.4; 206/581, 229, 223

[56] References Cited
U.S. PATENT DOCUMENTS

| | | | |
|---|---|---|---|
| 2,719,315 | 10/1955 | Sheehan | 15/210.1 |
| 2,736,913 | 3/1956 | Mirth | 15/122 |
| 3,568,237 | 3/1971 | Rhodes | 15/244 |
| 3,955,233 | 5/1976 | Nakamura | 132/320 X |
| 4,032,239 | 6/1977 | Maupin | 15/228 X |
| 4,176,420 | 12/1979 | Magid | 15/230 |
| 4,184,221 | 1/1980 | Edwards | 15/114 |
| 4,299,005 | 11/1981 | Brown | 15/244 |
| 4,381,766 | 5/1983 | Avolio | 15/210.1 X |
| 4,475,836 | 10/1984 | Colognori | 401/201 |
| 4,615,066 | 10/1986 | Colognori | 15/244 |
| 4,934,011 | 6/1990 | Haug | 15/145 |
| 5,003,659 | 4/1991 | Paepke | 15/244.1 X |
| 5,123,431 | 6/1992 | Wilson | 132/320 |

Primary Examiner—Jacob K. Ackun, Jr.
Attorney, Agent, or Firm—John L. Rogitz

[57] ABSTRACT

A device for applying skin treatment substances to the back of a person includes a manually grippable elongated shaft having a head formed thereon, and a plurality of contact pads, each selectively engageable with and disengageable from the head without damaging the head or pads. A first contact pad has a non-porous contact surface for applying relatively viscous substances to the skin of the person, a second contact pad has a porous contact surface for retaining relatively non-viscous substances for applying the relatively non-viscous substances to the skin of the person, and a third contact pad has a sisal contact surface for cleansing the skin of the person. Also, a fourth contact pad has an erose surface for gently scratching the person's back when rubbed against it. A bag is provided for holding the shaft and contact pads.

12 Claims, 2 Drawing Sheets

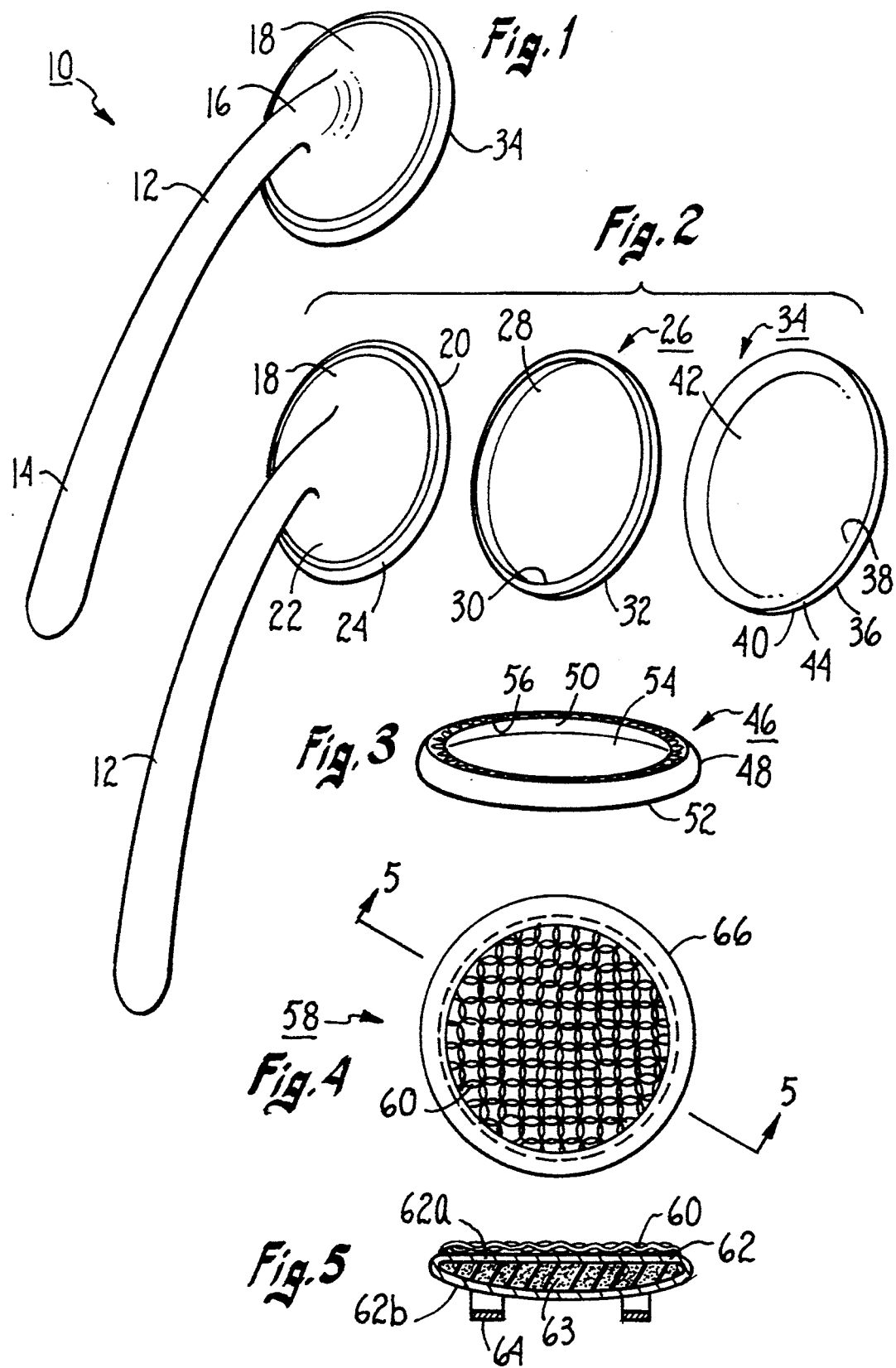

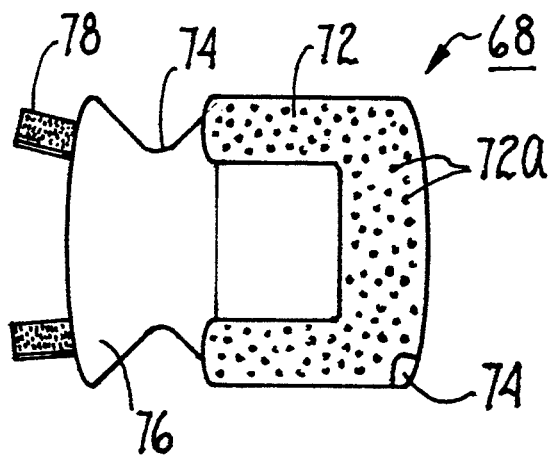
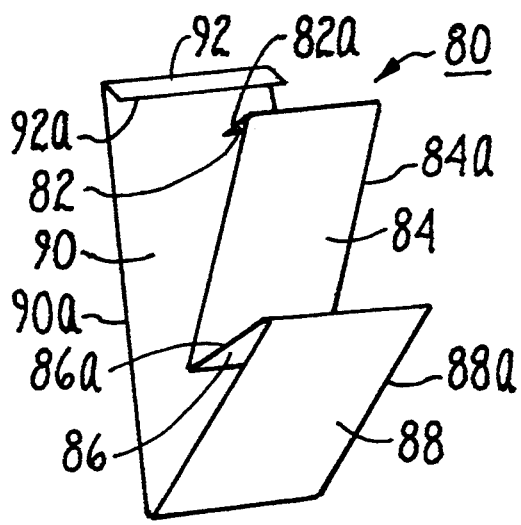
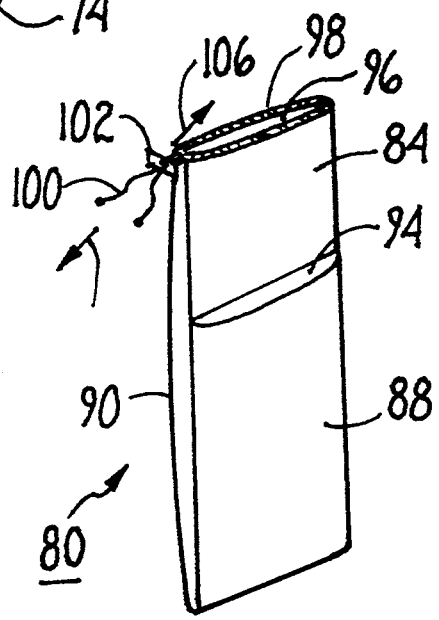
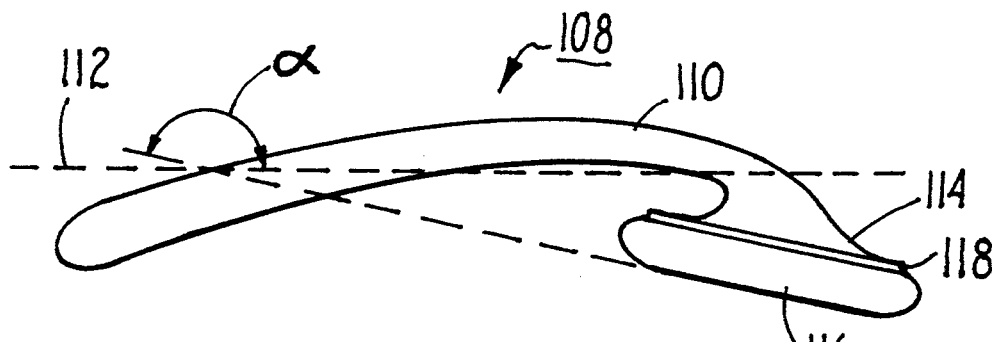

APPLICATOR DEVICE

FIELD OF THE INVENTION

The present invention relates generally to skin care products, and more particularly to devices for applying skin treatment substances to the back of a person.

BACKGROUND

Medical science continues to discover increasing evidence of the importance of proper skin care. For example, it has become clear that sunlight can damage a person's skin if the person's skin is repeatedly exposed to sunlight, i.e., if the person habitually remains outdoors without protective covering, e.g., clothing or suntan lotion. Such damage can include premature wrinkling and aging of the skin, and in some cases can lead to skin cancer.

While proper skin care can have remedial effects in alleviating or preventing skin damage, it can also have salubrious effects in restoring damaged skin and maintaining healthy skin. Not surprisingly, it may be desirable or necessary for a person to use a variety of skin treatment substances, depending on the particular need of the person and purpose of the skin treatment.

Accordingly, a large number of skin treatment substances are currently on the market. These substances include suntan lotions and oils, skin cleansers, skin conditioners, and so on. Typically, a person applies the desired skin treatment substance by hand, i.e., by rubbing the skin treatment substance into his or her skin.

Unfortunately, it can be difficult for a person to apply skin treatment substances to his or her own back, because it is anatomically difficult for most people to reach by hand large areas of their backs. Nevertheless, proper skin care of the back is important. Accordingly, it is not unusual for a person to receive assistance in applying skin care substances to his or her back, but such assistance is not always available or desired.

Accordingly, it is an object of the present invention to provide a device for enabling a person to personally apply skin treatments to his or her back. Another object of the present invention is to provide a device for enabling a person to apply a variety of skin care products to his or her back. Still another object of the present invention is to provide a device for proper skin care of the back which is easy to use and cost effective to manufacture.

SUMMARY OF THE INVENTION

An applicator device is disclosed for enabling a person to apply a skin treatment substance to hard-to-reach areas of the person's back. The device of the present invention includes an elongated shaft which has a first end and a second end, and the shaft includes a manually grippable segment formed adjacent the first end of the shaft. An applicator head having an applicator surface is formed on the second end of the shaft.

To cover the applicator surface of the head, a contact pad is removably engaged with the head. The contact pad can be manually removed from the head without damaging the head or pad and replaced with another contact pad.

Preferably, a resilient head pad is attached to the head for covering the applicator surface of the head. In the presently preferred embodiment, the contact pad has a flat cover portion which defines an inside surface, and the inside surface of the pad abuts the head pad. Also, the contact pad has a contact surface that is opposed to the inside surface of the pad for contacting the skin of the person.

As intended by the present invention, the contact pad has an opening and the opening has an elastic periphery. Consequently, the contact pad has an enlarged configuration, wherein the head can be moved through the opening to engage and disengage the contact pad from the head, and a gripping configuration, wherein the head cannot be moved through the opening, to thereby hold the contact pad onto the head. Preferably, the contact pad is materially biased to the gripping configuration.

Alternatively, the periphery of the opening of the contact pad is inelastic, and the pad has a flap which selectively covers the opening. The periphery can be held in the gripping configuration by fastening the flap over the opening using at least one fastener, e.g., a Velcro ® fastener.

To facilitate applying a variety of skin treatment substances to the back, a plurality of contact pads is preferably provided, with each pad being individually engageable with the head. Thus, a first contact pad has a non-porous contact surface for applying relatively viscous substances, e.g., suntan lotion or cream, to the back of a person. Also, a second contact pad has a porous contact surface for retaining relatively non-viscous substances, e.g., oil or alcohol, for applying the relatively non-viscous substances to the back of a person.

Yet a third contact pad has a Velcro ® contact surface for gently scratching the back of a person, and a fourth contact pad has a sisal contact surface for cleansing the back of a person.

In another aspect of the present invention, a device is manually grippable by a person to enable the person to apply a skin treatment substance to the person's back by touching the device to the person's back. The device includes a manually grippable elongated shaft and an enlarged head formed on the shaft. A contact pad is also provided, and the contact pad has a contact surface for holding the skin treatment substance. In accordance with the present invention, the contact pad has an enlarged configuration, wherein the pad can be manually engaged and disengaged with the head without damaging the pad or head, and a gripping configuration, wherein the pad is held onto the head. When the contact pad is in the gripping configuration, the person can manipulate the shaft to cause the contact pad to contact the person's back and thereby apply the skin treatment substance to the person's back. Advantageously, a bag can be provided for holding and carrying the shaft and the contact pads.

In yet another aspect of the present invention, an applicator kit is disclosed for applying a selectable one of a plurality of skin treatment substances to the skin of a person. The kit of the present invention includes a shaft having a head formed thereon. A first contact pad is engageable with the head, and the first pad has a non-porous contact surface for applying relatively viscous skin treatment substances to the skin of the person. Also, the kit includes a second contact pad engageable with the head, wherein the second pad has a porous contact surface for retaining relatively non-viscous skin treatment substances for applying the relatively non-viscous skin treatment substances to the skin of the person. Further, the kit includes a third contact pad engageable with the head, wherein the third pad has a sisal contact surface for cleansing the skin of the person. Additionally, the kit includes a bag having a first cavity for holding the shaft and a second cavity for holding the contact pads. One contact pad at a time can be selectively engaged and disengaged with the head without damaging the contact pad or the head.

In still another aspect of the present invention, an applicator device has an elongated shaft having a first end and a second end, and the shaft includes a manually grippable segment formed adjacent the first end of the shaft. An applicator head is formed on the second end of the shaft, and the head has an applicator surface. A contact pad is removably engaged with the head for covering the applicator surface. The pad has a contact surface made of a plastic abrasive material, such as Velcro ®, and the contact pad can be manually removed from the head without damaging the head or pad and replaced with another contact pad.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a perspective view of the applicator device of the present invention;

FIG. 2 is an exploded perspective view of the applicator device;

FIG. 3 is a perspective view of the oils and liniment applicator;

FIG. 4 is a top view of the cleansing applicator;

FIG. 5 is a cross-sectional view as would be seen along the line 5—5 in FIG. 4;

FIG. 6 is a perspective view of the back scratcher, with the flap in the open position;

FIG. 7 is a perspective view of the carrying bag of the present invention during manufacture;

FIG. 8 is a perspective view of the carrying bag of the present invention; and

FIG. 9 is a side view of an alternate embodiment of the applicator device of the present invention.

DETAILED DESCRIPTION OF THE PREFERRED EMBODIMENT

Referring initially to FIG. 1, an applicator device for applying skin treatment substances to a person's back is shown, generally designated 10. As shown, the device 10 includes an elongated manually grippable hollow shaft 12 having a handle segment 14 and a head end 16. The shaft 12 is gently curved along its dimension of elongation.

In cross-reference to FIGS. 1 and 2, a generally disc-shaped head 18 is formed on the head end 16 integrally with the shaft 12. The head 18 has a flat or slightly convex applicator surface 20, a rear surface 22 opposed to the applicator surface 20, and a periphery 24 established therebetween. As shown, the plane established by the applicator surface 20 is generally parallel to the longitudinal dimension of the shaft 12. Consequently, the applicator surface 20 can be positioned against the back of a person when the person grips the handle segment 14 and manipulates it appropriately.

Preferably, the shaft 12 and head 18 are made of a unitary piece of blow molded polyethylene. Other materials, however, e.g., polyurethane, polypropylene, other plastics, and wood, can also be used.

FIG. 2 best shows that a resilient head pad, generally designated 26, is positioned against the applicator surface 20 of the head 18 to cover the applicator surface 20. The head pad 26 is configured to conform to the head 18 and to tightly grip the head 18.

More specifically, the head pad 26 has an opening 28 defining an elastic periphery 30. It will be appreciated in reference to FIG. 2 that the periphery 30 of the resilient head pad 26 can be deformed slightly to permit positioning the applicator surface 20 of the head 18 through the opening 28 of the head pad 26 to abut a pad surface 32 of the head pad 26. As shown in FIG. 2, the pad surface 32 of the head pad 26 is shaped like the applicator surface 20 of the head 18.

Once the head pad 26 is positioned onto the head 18, the periphery 30 of the head pad 26 grips the rear surface 22 of the head 18 to tightly hold the head pad 26 onto the head 18.

Preferably, the head pad 26 is made of silicon having a durometer rating of twenty-five to forty-five (25–45) shore, and preferably thirty to forty (30–40) shore. Consequently, the head pad 26 can cushion the head 18, is durable and wear-resistant, and will not readily absorb skin treatment substances. Alternatively, the head pad 26 can be made of latex.

Still referring to FIG. 2, a non-porous, stretchable, preferably thin powdered latex lotion and cream contact pad, generally designated 34, is configured to conform to the head pad 26 and is removably attached to the head pad 26. As shown in FIG. 2, the lotion and cream contact pad 34 has a flat cover portion 36 which is configured like the pad surface 32 of the head pad 26, and the cover portion 36 defines an inside surface 38 which abuts the head pad 26. A contact surface 40 is opposed to the inside surface 38 for contacting the skin of a person.

Additionally, the lotion and cream contact pad 34 has an opening 42, and the opening 42 defines an elastic periphery 44 which is established by a roll of latex material formed integrally with the cover portion 36. Consequently, the lotion and cream contact pad 34 has an enlarged configuration, wherein the head pad 26 can be moved through the opening 42 to engage and disengage the lotion and cream contact pad 34 from the head pad 26, and a gripping configuration, wherein the periphery 44 of the pad 34 grips the head pad 26. With the contact pad 34 positioned on the head pad 26 in the gripping configuration, the head pad 26 cannot be moved through the opening 54. The lotion and cream contact pad 34 is thereby held onto the head 18. From the disclosure above, it is to be appreciated that the lotion and cream contact pad 34 is materially biased into the gripping configuration.

The skilled artisan will appreciate that by making the lotion and cream contact pad 34 from latex, the pad 34 imitates the feel of human skin, and will not readily absorb relatively viscous substances, e.g., suntan lotion and cream. The contact surface 52 of the lotion and cream contact pad 34 will, however, hold relatively viscous substances for applying such substances to human skin when the contact surface 52 is rubbed against the skin.

Also, latex is relatively inexpensive, so that the lotion and cream contact pad 34 can be a single use, disposable item for promoting hygiene. Thus, after use of the pad 34, the pad 34 manually can be moved to the enlarged configuration, manually removed from the head pad 26, and replaced by another like pad (not shown) for use of the applicator device 10 by another or the same person, without damaging either the pad 34 or head 18.

Now referring to FIG. 3, a single-use, disposable oil and liniment contact pad is shown, generally designated 46. It is to be understood that the oil and liniment contact pad 46 can be held onto the head pad 26 in place of the lotion and cream contact pad 34 to apply relatively non-viscous substances, e.g., body oil, alcohol, and liniment, to the skin of a person.

Accordingly, the oil and liniment contact pad 46 is made of a porous material, to enable the pad 46 to hold non-viscous substances. In one presently preferred embodiment, the oil and liniment contact pad 46 is made of a polypropylene cloth, e.g., the cloth material made by Kimberly-Clark Corp. and marketed under the trade designation "CREW WIPER 33330". Alternatively, the oil and liniment contact pad 46 can be made of another porous material, e.g., cotton cloth or cloth made of other suitable fabric.

As shown in FIG. 3, the oil and liniment contact pad 46 has a flat cover portion 48 which is configured like the pad surface 32 of the head pad 26, and the cover portion 48 defines an inside surface 50 which abuts the head pad 26. A contact surface 52 is opposed to the inside surface 50 for contacting the skin of a person.

Additionally, the oil and liniment contact pad 46 has an opening 54, and the opening 54 defines an elastic periphery 56. The periphery 56 of the opening 54 is established by a continuous elastic strip (not shown in FIG. 3), and the cover portion 48 is sewn to the elastic strip in a bunched configuration as is well-known in the art. Consequently, the oil and liniment contact pad 46 has an enlarged configuration, wherein the head pad 26 can be moved through the opening 54 to engage and disengage the oil and liniment contact pad 46 from the head pad 26, and a gripping configuration, wherein the periphery 56 of the pad 46 grips the head pad 26. With the contact pad 46 positioned on the head pad 26 in the gripping configuration, the head pad 26 cannot be moved through the opening 54. The oil and liniment contact pad 46 is thereby held onto the head 18. From the disclosure above, it is to be appreciated that the oil and liniment contact pad 46 is materially biased into the gripping configuration.

FIGS. 4 and 5 show a cleansing pad, generally designated 58, which can be attached to the head pad 26 in lieu of the pads 34, 46 disclosed above to cleanse and defoliate the skin of a person's back. As shown, the cleansing pad 58 has a scrubbing surface 60 which is made of a material that can scrub the skin of a person's back. In the presently preferred embodiment, the scrubbing surface 60 is made of knitted sisal.

As can best be appreciated in reference to FIG. 5, the scrubbing surface 60 is sewn to a terry cloth back 62. Preferably, the back includes a top layer 62a and a bottom layer 62b, and a sponge layer 63 is sandwiched between the layers 62a, 62b. The layers 62a, 62b of the terry cloth back 62 can be made from a unitary piece of cloth, or from separate pieces of cloth which are sewn together. Together, the terry cloth back 62 and sponge layer 63 can hold a cleansing substance, e.g., soapy water.

The cleansing pad 58 also includes a plurality of elastic straps 64, each of has two opposed ends attached to a periphery 66 of the back surface 62. Each strap 64 is distanced from the back surface 62 between the respective ends of the strap 64. Consequently, the elastic straps 64 can be manually deformed, and the head 18 with head pad 26 advanced between the elastic straps 64 and the back surface 62 of the cleansing pad 58. Then, the straps 64 are permitted to return to the biased configuration shown in FIG. 5 to hold the cleansing pad 58 onto the head pad 26. It is to be understood that the straps 64 can be omitted, and the periphery 66 elasticized in accordance with the principles discussed above regarding the oil and liniment contact pad 46, to hold the cleansing pad 58 onto the head pad 26.

FIG. 6 shows a back scratcher, generally designated 68, which can be attached to the head pad 26 in lieu of the pads 34, 46, 58 disclosed above to gently scratch the back of a person. As show, the back scratcher 68 has a contact surface 70 and a fastening surface 72 which is formed integrally with the contact surface 70 and folded back from the contact surface 70. Notches 74 are formed in the contact surface 70 to permit easily folding the fastening surface 72 back from the contact surface 70.

In the presently preferred embodiment, the contact surface 70 and fastening surface 72 are made of a plastic abrasive material, preferably Velcro ® hook type 88 material, for gently scratching human skin without unduly abrading the skin. As is known in the art, Velcro ® hook material consists of a plurality of tightly bunched, small plastic bristle-like hooks 72a. A flap 76 is formed integrally with the contact surface 70, and a plurality of fasteners 78 are attached to the flap 76. Each fastener is made of Velcro ® loop type 1000 material for engaging the Velcro ® hook material of the fastening surface 72.

Accordingly, the back scratcher 68 has an open configuration (shown in FIG. 6), wherein the fasteners 78 are distanced from the fastening surface 72 to permit positioning the head 18 with head pad 26 between the back surface 72 and the contact surface 70. Also, the back scratcher 68 has a closed configuration (not shown), wherein the fasteners 78 are attached to the fastening surface 72 to hold the back scratcher 68 onto the head 18 with head pad 26.

From the disclosure above, it is to be appreciated that any one of the pads 34, 46, 58, 68 can be manually individually engaged and disengaged with the head 18 without damaging the pads 34, 46, 58, 68 or head 18. Further, it is to be appreciated that because of the material of which it is made, the silicon head pad 26 has a high coefficient of friction, and the pads 34, 46, 58, 68 cannot consequently slide relative to the head pad 26 when the particular pad 34, 46, 58, 68 that is engaged with the head pad 26 is rubbed against human skin.

FIGS. 7 and 8 show that carrying bag, generally designated 80, can be provided for holding and transporting the shaft 12 and pads 34, 46, 58, 68 disclosed above. As can be appreciated in reference to FIG. 7, the bag 80 is preferably made from a single bolt of material. In the presently preferred embodiment, the bag 80 is made from a machine washable, water repellant, and protective material, e.g., the material marketed by Fabri-Quilt of North Kansas City, Mo., under the designation type 128 downproof rip-stop nylon material.

In cross-reference to FIGS. 7 and 8, the bag 80 has first through sixth panels 82, 84, 86, 88, 90, 92, and each panel 82, 84, 86, 88, 90, 92 has a respective edge 82a, 84a, 86a, 88a, 90a, 92a. The panels are folded relative to each other, as shown, and the edge 86a of the third panel 86 is sewn to the edge 84a of the second panel 84 to establish a first cavity 94. Also, the edges 84a, 88a of the second and fourth panels 84, 88 are sewn to the edge 90a of the fifth panel 90 to establish a second cavity 96. Further, the edges 82a, 92a of the first and sixth panels 82, 92 are respectively sewn to the second and fifth panels 84, 90 to establish a hollow peripheral border 98 of the second cavity 96. As shown in FIG. 7, the hollow peripheral border 98 has an open configuration, wherein the shaft 12 with head 18 can be advanced into the second cavity 96.

A drawstring 100 can be positioned within the hollow border 98, and the drawstring 100 is also operably engaged with a pull tab 102. Accordingly, the drawstring 100 can be pulled in the direction indicated by the arrow 104, and the pull tab 102 can be pulled in the direction indicated by the arrow 106, to move the border 98 to a closed configuration for enclosing the shaft 12 within the second cavity 96. On the other hand, the pads 34, 46, 58, 68 can be carried in the first cavity 94.

FIG. 9 shows that in an alternate embodiment, an applicator device 108 has an elongated shaft 110 roughly defining a longitudinal axis 112, and the device 108 further includes a disc-shaped head 114 having an applicator surface 116. The plane defined by the surface 116 establishes an oblique angle α of less than 180 degrees with respect to the axis 112. Stated differently, the surface 116 is inclined with respect to the axis 112 of the shaft 110. With this arrangement, a person is permitted to more easily position the surface 116 flush against the person's back when the person grips the shaft 110. If desired, a groove 118 can be formed on the head 114 to provide a seating surface for the periphery 44 of the contact pad 34 shown in FIGS. 1 and 2.

While the particular applicator device as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. An applicator device, comprising:
   an elongated shaft having a first end and a second end, the shaft including a manually grippable segment formed adjacent the first end of the shaft;
   an applicator head formed on the second end of the shaft, the head having an applicator surface;
   a non-porous contact pad removably engaged with the head for covering the applicator surface, wherein the contact pad is formed with an opening and is movable between an enlarged configuration, wherein the head can be moved through the opening to engage and disengage the contact pad from the head, and a gripping configuration, wherein the head cannot be moved through the opening, to thereby hold the contact pad onto the head; and
   a resilient head pad attached to the head for covering the applicator surface of the head, the head pad being formed with a continuous outer surface for abutting the contact pad and substantially preventing relative motion between the contact pad and head pad.

2. The applicator device of claim 1, wherein the contact pad has a flat cover portion defining an inside surface abutting the head pad and a contact surface opposed to the inside surface for contacting the skin.

3. The application device of claim 2, wherein the contact pad is materially biased to the gripping configuration.

4. The applicator device of claim 3, wherein the contact pad is held in the gripping configuration by at least one fastener.

5. The applicator device of claim 2, wherein the applicator device is a kit, and the device further comprises a plurality of contact pads, each pad being individually engageable with the head.

6. The applicator device of claim 5, wherein a first contact pad has a non-porous contact surface for applying relatively viscous substances to the back of a person, a second contact pad has a porous contact surface for retaining relatively non-viscous substances for applying the relatively non-viscous substances to the back of a person, a third contact pad has a Velcro ® contact surface for gently scratching the back of a person, and a fourth contact pad has a sisal contact surface for cleansing the back of a person.

7. A device manually grippable by a person to enable the person to apply a skin treatment substance to the person's back by touching the device to the person's back, comprising:
   a manually grippable, curved elongated shaft:
   an enlarged head formed on the shaft;
   a resilient head pad attached to the head for covering the head, the head pad being formed with a continuous outer surface; and
   a plurality of contact pads, each contact pad being individually engageable with the head pad, each contact pad having a contact surface for holding the skin treatment substance, each contact pad having an enlarged configuration, wherein the contact pad can be manually engaged and disengaged with the head, and a gripping configuration, wherein the contact pad is held onto the head, such that the person can manipulate the shaft to cause the contact pad to contact the person's back and thereby apply the skin treatment substance to the person's back.

8. The device of claim 7, wherein a first contact pad has a non-porous contact surface for applying relatively viscous substances to the skin of the person, a second contact pad has a porous contact surface for retaining relatively non-viscous substances for applying the relatively non-viscous substances to the skin of the person, and a third contact pad has a sisal contact surface for cleansing the skin of the person.

9. The device of claim 8, further comprising a bag having a first cavity for holding the shaft and a second cavity for holding the contact pads.

10. An applicator kit for applying a selectable one of a plurality of skin treatment substances to the skin of a person, comprising:
    a shaft having a head formed thereon;
    a first contact pad engageable with the head, the first pad having a non-porous contact surface for applying relatively viscous skin treatment substances to the skin of the person;
    a second contact pad engageable with the head, the second pad having a porous contact surface for retaining relatively non-viscous skin treatment substances for applying the relatively non-viscous skin treatment substances to the skin of the person; and
    a third contact pad engageable with the head, the third pad having a sisal contact surface for cleansing the skin of the person.

11. The kit of claim 10, further comprising:
    a bag having a first cavity for holding the shaft and a second cavity for holding the contact pads, wherein one contact pad at a time can be selectively engaged and disengaged with the head without damaging the contact pad or the head.

12. An applicator device, comprising:

an elongated curved shaft having a first end and a second end, the shaft including a manually grippable segment formed adjacent the first end of the shaft;

an applicator head formed on the second end of the shaft, the head having an applicator surface;

a first contact pad engageable with the head, the first pad having a non-porous contact surface for applying relatively viscous skin treatment substances to the skin of the person;

a second contact pad engageable with the head, the second pad having a porous contact surface for retaining relatively non-viscous skin treatment substances for applying the relatively nonviscous skin treatment substances to the skin of the person;

a third contact pad engageable with the head, the third pad having a sisal contact surface for cleansing the skin of the person; and a scratch pad non-adhesively engaged with the head for covering the applicator surface, the pad having a contact surface made of plastic hook material, wherein the scratch pad can be manually removed from the head without damaging the head or pad and replaced with another pad.

* * * * *